United States Patent [19]

Roberts

[11] Patent Number: 4,553,939
[45] Date of Patent: Nov. 19, 1985

[54] TOOL FOR FORMING A RECESS FOR A DENTAL IMPLANT

[76] Inventor: Harold D. Roberts, 8115 Adera, Vancouver, B.C., Canada, V6P 5E4

[21] Appl. No.: 625,214

[22] Filed: Jun. 27, 1984

[51] Int. Cl.[4] .............................................. A61C 3/02
[52] U.S. Cl. .................................... 433/144; 433/141; 433/176
[58] Field of Search ................ 433/144, 141, 143, 176

[56] References Cited

U.S. PATENT DOCUMENTS

| 1,674,547 | 6/1928 | Hayden | 433/141 |
| 2,056,417 | 10/1936 | Bosworth | 433/144 |
| 2,154,751 | 4/1939 | Hoskins | 433/144 |

Primary Examiner—John J. Wilson
Attorney, Agent, or Firm—Eugene M. Eckelman

[57] ABSTRACT

A tool with a gripping handle and a forwardly extending shank on the handle having a cross sectional dimension of height and thickness capable of being received in a primary recess in the ramus portion of a mandible. A reduced thickness extension is provided on the forward end of the shank which is arranged to form a reduced width secondary recess by manually forcing the extension into the bone area at an end of the primary recess. The shank has an upwardly angled forward portion and the handle has a rearward angled end forming a lateral gripping area for the tool. The free end of the extension is rounded and sharpened for piercing bone.

4 Claims, 4 Drawing Figures

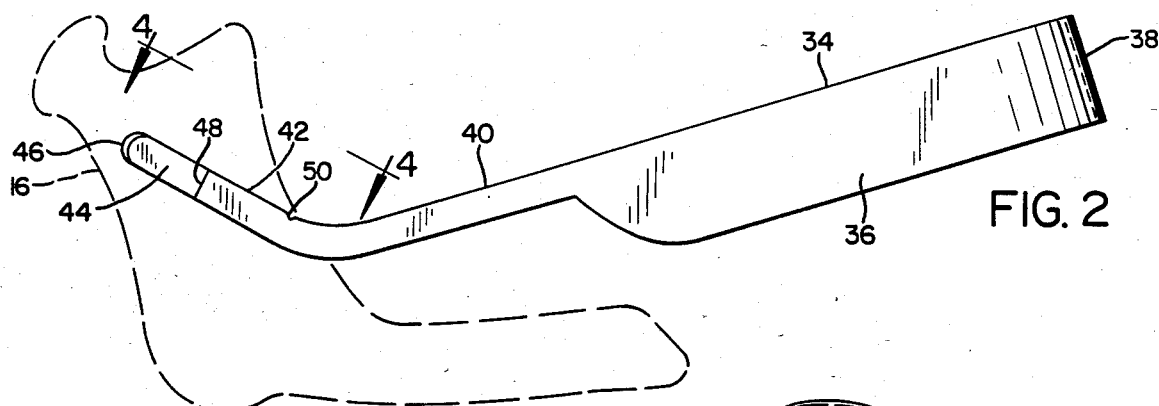
FIG. 2
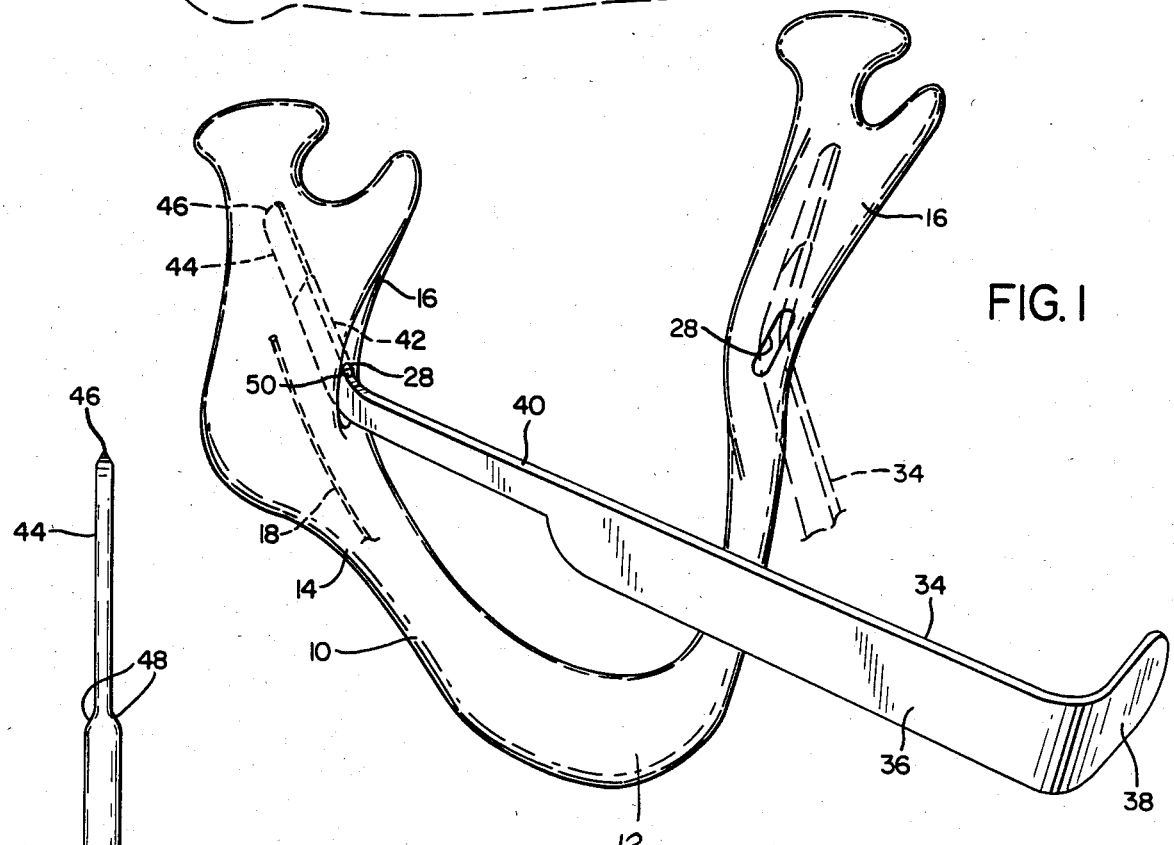
FIG. 1
FIG. 4
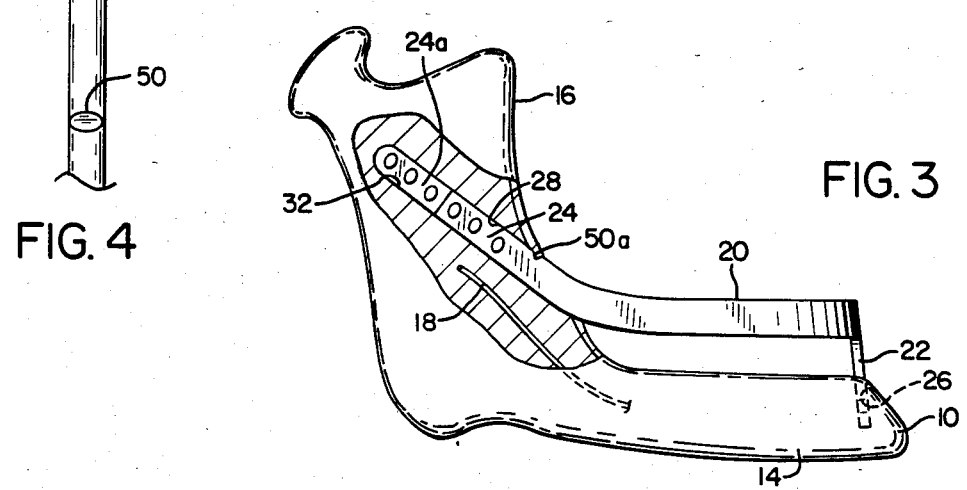
FIG. 3

TOOL FOR FORMING A RECESS FOR A DENTAL IMPLANT

BACKGROUND OF THE INVENTION

This invention relates to new and useful improvements in dental tools and particularly pertains to a tool for forming a recess adapted to receive a dental implant.

Dental implants have for some time been used for anchoring support bars for artificial dentures, and such implants include blades or the like installed in the ramus portions of the mandible. Such ramus portions have an outer defining layer of hard corticle bone and intermediate soft spongy bone, and implants hereinbefore installed in the ramus portions are seated in recesses provided in the soft spongy bone at the forward end of the ramus portions. It has been known to force portions of the implant into the soft spongy bone beyond a prepared recess whereby a partial connection is provided in the ramus portions instantaneously. Such is accomplished without the use of tools since a tool has not been available to perform the necessary work.

The forward area of the ramus portions is substantially wide as viewed from the front but the ramus portions taper rearwardly to a narrower dimension, namely, a dimension not capable of receiving implants of a width equal to that of the usual implant blade. I propose, as set forth in my copending application, Ser. No. 627,079, Filed July 2, 1984, to provide a thinned or secondary extension of a primary recess provided in the forward part of the ramus portion for receiving a thinned extension on an implant whereby to establish, by means of such secondary recess, an implant in the rear narrow area of the ramus portion.

SUMMARY OF THE INVENTION

According to the present invention and forming an objective thereof, a tool is provided which is arranged to form a recess in the ramus portions to receive an implant that can extend back into the rear thin portion of the ramus portions, such tool for the intended purpose having a gripping handle, a shank, and an extension on the shank arranged to form or partially form the recess. The tool is arranged to form the recess by manually forcing it into the bone at the ramus portion. The shank of the tool has an upwardly angled forward portion which permits the dentist to work at the proper angle. The tool has a laterally angled portion at the other end forming a hand grip portion.

The invention will be better understood and additional objects and advantages will become apparent from the following description taken in connection with the accompanying drawings.

BRIEF DESCRIPTION OF THE DRAWINGS

FIG. 1 is a perspective view of the present tool and a mandible, the tool being shown in position in the mandible for forming a recess to receive a ramus implant portion;

FIG. 2 is a side elevational view of the tool and a mandible, the mandible in this view being shown in broken lines;

FIG. 3 is a side elevational view of a mandible and a denture support bar mounted thereon, a portion of the mandible being broken away to show the internal implant; and FIG. 4 is a fragmentary plan or edge view of the tool.

DETAILED DESCRIPTION OF A PREFERRED EMBODIMENT

The numeral 10 designates a mandible or lower jaw bone of a person. Such mandible has a curved front end 12, substantially straight side portions 14, and rear ramus portions 16. These ramus portions extend upwardly for hinged connection to the skull. The lower forward areas of the ramus portions are quite wide as viewed from the front but the upper and rear areas taper to a thinner dimension. An outer defining shell or layer of the ramus portions comprises hard corticle bone whereas the area between these defining sides is soft and spongy. The rear area of the ramus portions will not generally take an implant of the usual width, this being particularly the case in older persons wherein there is atrophy to the bone. The alveolar nerve 18 enters at about halfway between the upper and lower ends of the ramus portions and along the mandible.

With particular reference to FIG. 3, denture support bars 20 in a known manner have been secured to the mandible 10 by a front implant 22 and a rear implant 24. To install the implant 22 a suitable recess 26 is cut in the front of the mandible, and to install the implants 24, suitable recesses 28 are cut in the ramus portions. With the implants 24 and 26 thusly installed, bone growth of the soft spongy bone rapidly secures them in place.

It is proposed, as set forth in my co-pending application above-mentioned, to extend an implant portion rearwardly into the rear thin area of the ramus portions 16, and for this purpose thinned implant portions 24a extend from the implants 24 and are sufficiently thin to be received in the rear thin spongy bone area of the ramus portions. However, it has not been practical by existing tools to provide a secondary recess or at least a partial secondary recess for receiving the thinned end 24a since drilling tools are available to form recess 24 but not recesses therebeyond. It is sometimes desired that this thin end 24a of the implant be partially forced into the spongy bone to form its own recess but it may be necessary to at least start this recess whereby the end of the implant portion 24a is directed properly in the right direction. Then it can be forced the rest of the way. The numeral 32 designates the secondary recess into which the implant portion 24a is contained.

For the purpose of forming the recess 32, or a portion thereof, a tool 34 is provided, FIGS. 1, 2 and 4, according to the present invention. This tool has a handle 36 with a rear laterally turned end 38. It has a vertical body height of sufficient dimension to provide a good grip thereon. The rear turned end 38 assists in the grip. The forward end of the tool comprises a reduced height shank 40 having an upwardly angled front portion 42. The height dimension of the upwardly angled portion 42 and its width or thickness dimension corresponds with or is slightly smaller than the dimensions of the recess 28 whereby this portion of the tool is readily received in the recess 28. A representative dimension of the portion 42 is 5 mm. in height and 2 mm. in width or thickness. The upward angle of the portion 42 relative to the shank 40 may vary but preferably is approximately 20 degrees. The angled portion 42 terminates in a narrowed or thinned end 44 which in a customary size is about 1 mm. in width or thickness and of suitable length such as about 15 to 20 mm. The terminal end 46 of the portion 44 is rounded from top to bottom and also sharpened to a knife edge such that with slight manipulation the portion 44 can be forced into the bone. The juncture between the portions 42 and 44 forms opposite shoulders 48 which limit penetration of the portion 44 into the bone.

The thinned end 44, as stated, is for the purpose of starting or fully forming the thinned recess 32 for the implant portion 24a, and one form of preparation for this special ramus implant is as follows. A primary recess 28 is first cut by a suitable tool at the desired angle, height, width and depth for receiving the implant portion 24 of the bar. Thereupon, the tool 34 is used to form a secondary recess 32 or partially form this recess such that the implant portion 24a can be installed in the thinned rear area of the ramus portions. With a good grip on the tool, the dentist can force the thinned portion 44 of the tool into the bone to make or at least start the recess 32. The tool can be manipulated to form a full size recess or it can be manipulated to form only a partial recess whereby a portion of the implant 24a must be forced into place in the bone to provide an instantaneous connection. Suitable marking means 50 may be employed on the top edge of the tool for measuring the amount of penetration. The mark 50 can be associated with a mark 50a on the bar 20 for providing the desired depth of operation of the tool.

In the installation of the bar 20, the rear implant ends 24a are directed into the recesses 28 and the bar 20 moved rearwardly. As the bar moves rearwardly, the thinned portions 24a are directed into the recesses 32 which have been formed by the present tool. If such recesses have only been partially formed by the tool, the thin portions 24a cut their own path rearwardly by manually forcing the bar in that direction. Rearward movement of the bar is continued until the front implant 22 can be placed in the recess 26.

With the sharpened and rounded edge 46 of the tool portion 44, it is sometimes possible to provide the entire bone opening for receiving the implant portions 24 and 24a, namely, this sharpened end can actually pierce the corticle bone at the front of the ramus portions and the interior bone to the desired depth. Thus, in some cases, drilling will not be necessary and this can have some advantages, for example, there is no heat developed by drills and the like and small nerves are merely displaced rather than severed.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A tool for forming a reduced-width secondary recess as an extension of a primary recess in a ramus portion of a mandible for the purpose of installing a reduced-width portion of an implant in the secondary recess, said tool comprising a gripping handle, a forwardly extending shank on said handle having an upwardly angled forward portion, said forward portion having a cross sectional dimension of height and thickness capable of being received in a primary recess which has been cut in the ramus portion, and an extension of reduced thickness on the forward end of said shank arranged to form the reduced width secondary recess by manually forcing said extension into bone area at an end of the primary recess, said upwardly angled forward portion having a thickness of approximately 2 mm. and said reduced thickness extension having a thickness of approximately 1 mm.

2. The tool of claim 1 wherein said shank has a laterally angled rearward end forming a lateral grip thereon.

3. The tool of claim 1 wherein said extension terminates in a rounded and sharpened end for piercing bone.

4. The tool of claim 1 including indicating means on said upwardly angled forward portion capable of use as a guide for the depth of penetration to be made by said reduced thickness extension in the bone.

* * * * *